US012727926B2

(12) United States Patent
Siccardi et al.

(10) Patent No.: US 12,727,926 B2
(45) Date of Patent: Sep. 8, 2026

(54) GRIPPING AND POSITIONING TOOL FOR A SPINAL POLY-AXIAL SCREW INSERTION GUIDE

(71) Applicant: MEDACTA INTERNATIONAL SA, Castel San Pietro (CH)

(72) Inventors: Francesco Siccardi, Castel San Pietro (CH); Meinrad Fiechter, Castel San Pietro (CH); Yuri Insinna, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 615 days.

(21) Appl. No.: 17/436,166

(22) PCT Filed: Feb. 27, 2020

(86) PCT No.: PCT/IB2020/051676
§ 371 (c)(1),
(2) Date: Sep. 3, 2021

(87) PCT Pub. No.: WO2020/178678
PCT Pub. Date: Sep. 10, 2020

(65) Prior Publication Data

US 2022/0133366 A1 May 5, 2022

(30) Foreign Application Priority Data

Mar. 5, 2019 (IT) ........................ 102019000003147

(51) Int. Cl.
*A61B 17/70* (2006.01)
*A61B 17/00* (2006.01)

(52) U.S. Cl.
CPC ............................... *A61B 17/7083* (2013.01); *A61B 2017/00424* (2013.01); *A61B 2017/00477* (2013.01);
(Continued)

(58) Field of Classification Search
CPC .. A61B 17/1757; A61B 17/7074–7092; A61B 17/808
See application file for complete search history.

(56) References Cited

U.S. PATENT DOCUMENTS 4,981,143 A * 1/1991 Sakita ................ A61B 10/0291 600/570
5,010,658 A * 4/1991 Griffith .................. G01B 7/282 33/784
(Continued)

FOREIGN PATENT DOCUMENTS

EP 3210550 A1 8/2017
JP 2017131662 A 8/2017
(Continued)

OTHER PUBLICATIONS

International Search Report and Written Opinion, issued by the International Searching Authority (ISA/EP) in PCT Application No. PCT/IB2020/051676 on Jul. 6, 2020. 15 pages.
(Continued)

*Primary Examiner* — Eduardo C Robert
*Assistant Examiner* — Steven J Cotroneo
(74) *Attorney, Agent, or Firm* — Meunier Carlin & Curfman LLC

(57) ABSTRACT

A gripping and positioning tool for a poly-axial screw insertion guide comprises a handle, a main body connected to the handle positioned at a first end of the main body and a coupling zone positioned at a second end of the main body. The coupling zone is able to vary its position with respect to the insertion guide keeping the application direction of the force applied by the surgeon to said instrument constant.

6 Claims, 5 Drawing Sheets

(52) U.S. Cl.
CPC ............... *A61B 2017/00902* (2013.01); *A61B 2017/0092* (2013.01)

(56) References Cited

U.S. PATENT DOCUMENTS

| | | | | |
|---|---|---|---|---|
| 5,014,444 | A * | 5/1991 | Breyer | G01B 5/0014 33/502 |
| 9,642,633 | B2 * | 5/2017 | Frey | A61B 50/33 |
| 10,159,475 | B2 * | 12/2018 | Frey | A61B 17/70 |
| 10,376,374 | B2 * | 8/2019 | Biedermann | A61F 2/442 |
| 11,123,117 | B1 * | 9/2021 | Sweeney | A61B 17/809 |
| 2004/0023187 | A1 * | 2/2004 | Hickok | A61C 3/03 433/119 |
| 2004/0204717 | A1 * | 10/2004 | Fanger | A61B 17/1757 606/96 |
| 2006/0084986 | A1 * | 4/2006 | Grinberg | A61F 2/4684 606/279 |
| 2009/0187194 | A1 * | 7/2009 | Hamada | A61B 17/7001 606/104 |
| 2010/0100138 | A1 * | 4/2010 | Reynolds | A61B 17/7059 606/86 A |
| 2010/0286710 | A1 * | 11/2010 | Boyer | A61B 34/20 606/130 |
| 2011/0213376 | A1 * | 9/2011 | Maxson | A61B 17/152 606/88 |
| 2011/0230965 | A1 * | 9/2011 | Schell | A61B 17/7064 606/86 A |
| 2013/0123793 | A1 * | 5/2013 | Kehres | A61B 17/00 606/104 |
| 2013/0150906 | A1 * | 6/2013 | Kerboul | A61B 17/808 606/86 A |
| 2013/0218163 | A1 * | 8/2013 | Frey | A61B 17/1671 606/86 R |
| 2015/0201975 | A1 | 7/2015 | Paul | |
| 2017/0056194 | A1 * | 3/2017 | Biedermann | A61F 2/4465 |

FOREIGN PATENT DOCUMENTS

| | | | |
|---|---|---|---|
| WO | 2014/085870 | A1 | 6/2014 |
| WO | 2018/071627 | A1 | 4/2018 |
| WO | 2018/098090 | A1 | 5/2018 |

OTHER PUBLICATIONS

Notice of Reasons of Refusal received in JP 2021-552523 with English Translation, mailed Oct. 20, 2022, 8 pages.

* cited by examiner

GRIPPING AND POSITIONING TOOL FOR A SPINAL POLY-AXIAL SCREW INSERTION GUIDE

TECHNICAL FIELD

This invention concerns a gripping and positioning tool for a spinal poly-axial screw insertion guide.

PRIOR ART

Currently, spinal surgery guides designed for inserting poly-axial screws are provided with gripping handles or bridges designed to enable the surgeon to hold the guide firmly in the correct position during the various stages of surgery.

This structure, although widely used for years in spinal surgery guides, is nevertheless difficult to use, especially in obese patients with a particularly thick layer of soft tissue that hinders the view of the surgical field or in cases where maneuverability at greater distance is required. In addition, known devices are difficult to use during minimally invasive procedures, where it is the incision made in the patient's skin needs to be minimised, creating the smallest possible surgical site.

The current devices do not have any auxiliary handle that would make it possible to keep the guide in the correct position on the patient during the entire surgical phase from a given distance and with greater and improved ergonomics.

In addition, the current guides are of little use in minimally invasive surgery, as there must be adequate space to permit the surgeon to keep their grip on the guide itself.

In addition, the pressure that the surgeon exerts on the handle or bridge, integrated into the guide, may change direction depending on the direction of thrust that the surgeon exerts on the gripping element. This can lead to potential imbalance or destabilisation of the guide itself during surgery.

The surgeon must, in fact, move the force application direction to operate on an insertion sleeve to avoid obstructing the field of vision with their hands.

The purpose of this invention is to overcome the drawbacks of the prior art.

In particular, the purpose of this invention is to propose a gripping and positioning tool for a spinal poly-axial screw insertion guide that enables the easy gripping and correct maintenance of the most suitable position of the guide itself, being able to control and keep constant the application direction of the force on the guide itself.

An additional purpose of this invention is to provide a gripping and positioning tool for a spinal poly-axial screw insertion guide that does not obstruct the surgeon's field of vision.

Finally, the purpose of this invention is to propose a gripping and positioning tool for a spinal poly-axial screw insertion guide that makes it possible to control the stability of the guide even at a distance, so that X-rays or fluoroscopy can be performed without the obstacle posed by the presence of the surgeon's hand.

These and other purposes and advantages are achieved with a gripping and positioning tool for a spinal poly-axial screw insertion guide according to what is described in the appended claims.

SUMMARY

A first aspect of this invention provides a gripping and positioning tool for a spinal poly-axial screw insertion guide comprising a main body extending entirely along a straight longitudinal axis, a handle for grasping the tool that is positioned at a first end of the main body, and a coupling zone that is positioned at a second end of the main body and configured to couple inside a housing made on said spinal guide.

The handle and the coupling zone are connected in axial alignment with the main body to form a single body with a straight axial extension. The coupling zone, thanks to this axial alignment, is able to vary its position in relation to the insertion guide, keeping the application direction of the force applied by the surgeon to the tool constant.

The coupling zone is of the spherical type. The coupling zone advantageously comprises a spherical joint.

The main body has ergonomic grooves to facilitate the handling of the tool, even in the presence of body fluids.

The handle preferably defines a T with the main body.

The whole tool is made of radiolucent material.

BRIEF DESCRIPTION OF THE FIGURES

A gripping and positioning tool for a spinal poly-axial screw insertion guide as described and claimed is also illustrated in the following figures that are intended to be illustrative and not exhaustive, wherein:

FIG. 1 is a perspective view of a gripping and positioning tool for a spinal poly-axial screw insertion;

DETAILED DESCRIPTION

Figure 2:
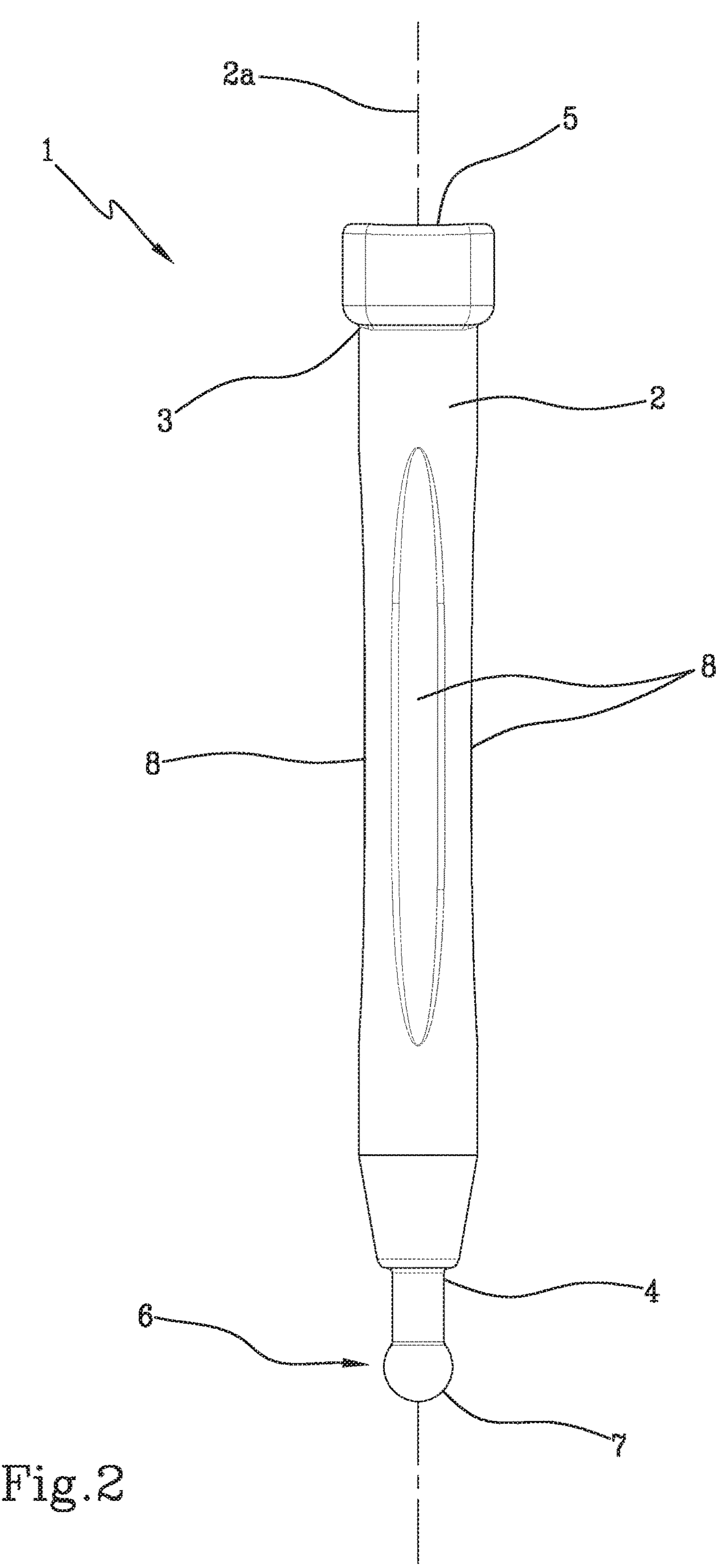
FIG. 2 is a front view of the tool in FIG. 1.
Figure 3:
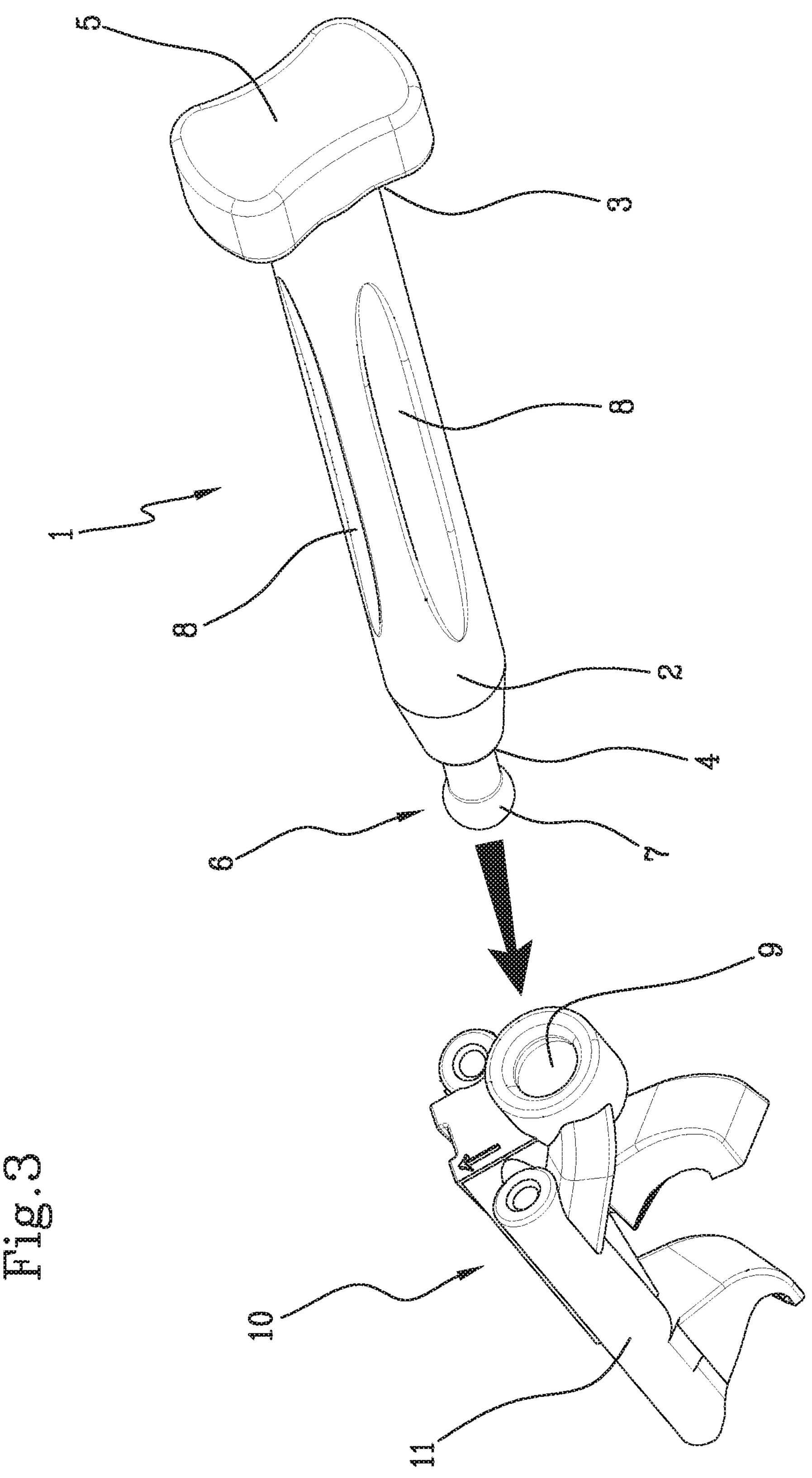
FIG. 3 is a perspective view of the gripping and positioning tool, the subject of this invention, in a coupling phase with a spinal surgery guide.
Figure 4:
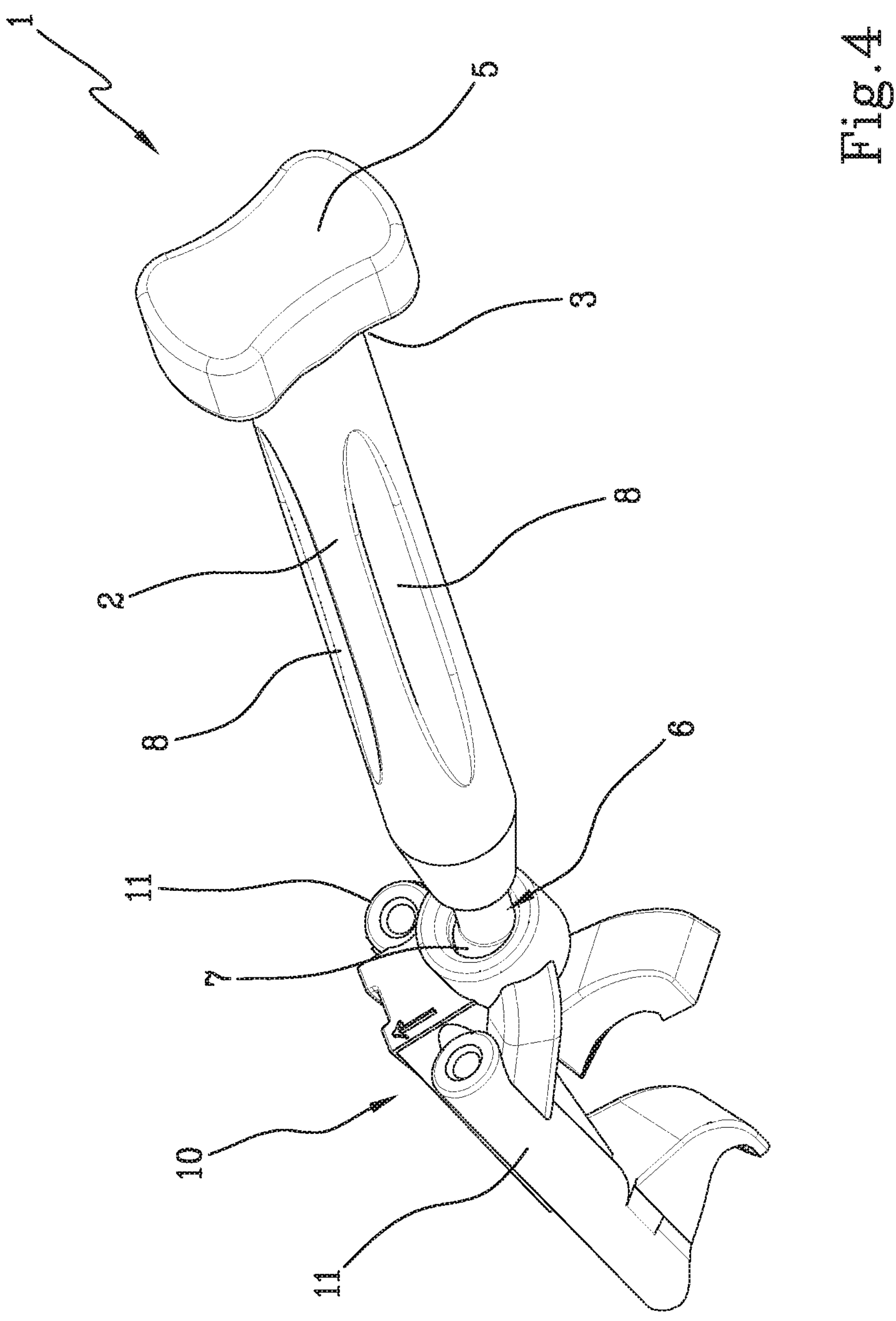
FIG. 4 is a perspective view of the gripping and positioning tool joined to a spinal guide.

With reference to the attached figures, the reference number 1 indicates a gripping and positioning tool for a spinal poly-axial screw insertion guide 10 according to this invention.

The gripping and positioning tool 1 comprises a main body 2 that extends along a straight longitudinal axis **2*a* and has a first end 3 and a second 4** end.

The gripping and positioning tool 1 also comprises a handle 5 connected to the first end 3 of the main body 2.

The handle 5, which is designed to enable the surgeon to grasp the tool 1, is connected in axial alignment to the main body 2. The handle 5 is preferably transverse to the longitudinal axis **2*a* of the main body, defining a T with the latter. The central axis of the handle 5 coincides with the longitudinal axis 2*a* of the main body 2**.

At the second end 4 of the main body 2, the tool 1 has a coupling zone 6 to connect the gripping tool to a spinal poly-axial screw insertion guide 10, for use in spinal surgery.

The coupling zone 6 is also connected in axial alignment to the main body 2.

The coupling zone 6 is also configured to be inserted inside a housing made on the spinal poly-axial screw insertion guide.

The coupling zone 6 is, advantageously, able to vary its position in relation to the insertion guide, keeping the application direction of the force applied by the surgeon to the tool constant. This is possible precisely because of the axial alignment between the handle 5, main body 2, and coupling zone 6 that create, thus, a single body with a straight axis.

The coupling zone 6 preferably has a spherical type shape, in particular it comprises a spherical joint 7.

The housing made on the spinal poly-axial screw insertion guide is counter-shaped to the coupling zone, so as to accommodate the latter and enable it to move without any risk of its becoming disengaged. To remove the gripping and positioning tool 1, the surgeon must apply a tensile force to disengage the spherical joint 7 from the spinal guide housing.

Figure 1:
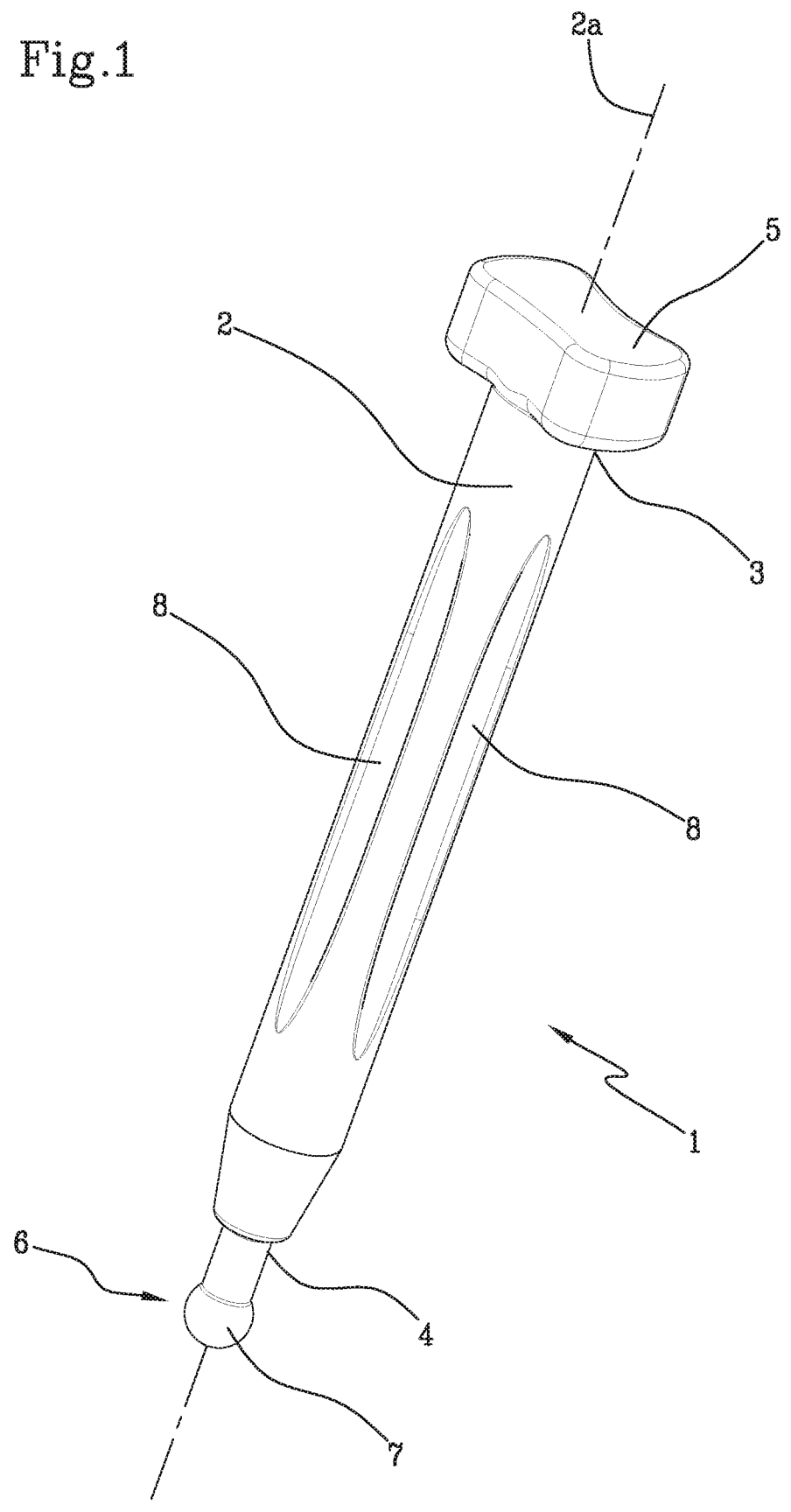

The main body 2 has ergonomic grooves 8 (FIGS. 1 and 2) that facilitate the handling of the tool 1, even in the presence of body fluids.

The whole gripping and positioning tool 1 is advantageously made of radiolucent material, so that it can remain connected to the guide even during operations such as X-ray imaging or fluoroscopy.

In use, once the spinal surgery guide 10 has been positioned, it couples with the gripping and positioning tool 1 via the spherical joint 7 located in the coupling zone 6 of the tool 1, located at the second end 4 of the main body 2. The spherical joint 7 is inserted inside a recess or seat 8 in the guide 10 itself.

The surgeon couples the tool 1 with the guide 10 by inserting, preferably by interference, the coupling zone 6, specifically the spherical joint 7, inside the housing made on the spinal surgery guide 10.

Once coupled to the guide 10, the tool 1 can rotate in relation to the guide itself, as directed by the surgeon. This is possible thanks to the spherical joint between the tool and the guide.

In this way, the surgeon is able to keep the application direction of the force on the tool constant, and thus on the guide, avoiding destabilising the guide from the correct position on the spine. The surgeon is also able to direct and keep the force application direction constant thanks to the single-body configuration of the whole tool, which is aligned along a straight axis.

The spherical joint 7 connection provides two advantages: the first is that it is possible to move the handle when operating on the guide so that the handle itself is not in the direction of the poly-axial screw insertion sleeves 11, so as not to disturb the surgeon when inserting the Kirchner wires or screws. However, thanks to the spherical coupling, while varying the position of the handle in relation to the guide, it will be possible to continue to exert a control force on the guide itself that is forced to stay in the correct position.

The purpose of this tool is to keep the spinal surgery guide in the correct position, without the surgeon's needing to place their hand directly on the guide.

The spherical connection enables engagement with the guide, in the appropriate recess or seat 9 on the guide itself, and leaves the tool a degree of rotational freedom (possibility of movement to describe a cone) necessary to avoid possible interference with other tools.

The handle 5 makes it easy to hold the tool 1 only from the end during lumbar puncture and the acquisition of X-rays or fluoroscopy, so as not to interfere with the surgical site.

Figure 5:
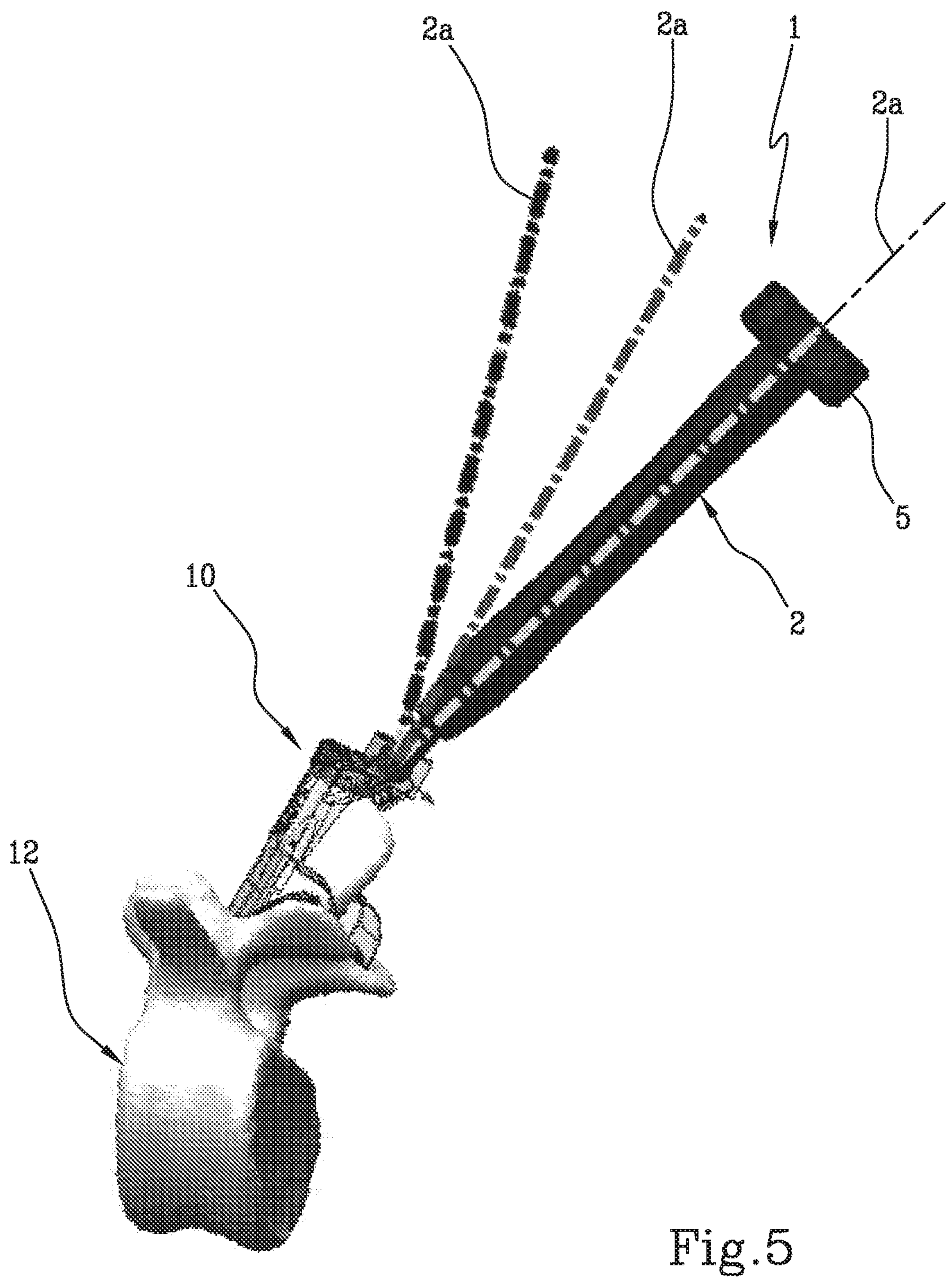
FIG. 5 is a view of the gripping and positioning tool, connected to a spinal guide joined to a spinal vertebra, in which some possible inclinations of the tool itself, in relation to the spinal guide, are shown.

The main innovation lies, therefore, in the possibility of having a mobile handle: it is possible to rotate the tool without changing the positioning of the spinal guide thanks to the spherical connection and this guarantees the guide's stability. The gripping and positioning tool can, thus, rotate according to a circular trajectory that defines a cone in space. FIG. 5 shows a possible angle for moving and orienting the tool connected to the spinal guide 10 joined to a vertebra 12. The positions of the longitudinal axes 2*a* are outlined in dashes.

The tool 1 also enables the surgeon to hold the spinal guide in position, while keeping their hand out of the radiation field of the fluoroscopy or x-ray when checking the trajectory of the potential screw.

The tool is very useful when performing minimally invasive techniques (small incisions) and when the patient is obese (maximum presence of soft tissue).

The problem solved by this invention is, thus, to provide an auxiliary handle that makes it possible to keep the guide in the correct position on the patient during the entire surgical phase from a given distance and with greater and improved ergonomics.

The invention claimed is:

1. A kit for holding and positioning a spinal poly-axial screw insertion guide comprising:

a gripping and positioning tool comprising:

a main body extending along a longitudinal axis and having a first end and a second end;

a handle coupled to the first end of said main body; and a spherical joint disposed at a terminal end of the second end of said main body, wherein said main body extends entirely along said longitudinal axis, said handle and said spherical joint being in axial alignment with said main body, and wherein said spherical joint is configured for varying an angular position of the longitudinal axis of the main body with respect to the spinal poly-axial screw insertion guide while keeping an application direction of the applying force to the handle of the spinal poly-axial screw insertion guide constant when the gripping and positioning tool is used to grip and position a spinal poly-axial screw insertion guide, wherein the spherical joint comprises a central axis, and at least a portion of an outer surface of the spherical joint intersects the central axis; and a spinal poly-axial screw insertion guide comprising a housing defining a semispherical recess counter-shaped to the spherical joint of the gripping and positioning tool, wherein the spherical joint is configured to be directly coupled with and disposed within the semispherical recess of the spinal poly-axial screw insertion guide when the gripping and positioning tool is used to grip and position the spinal poly-axial screw insertion guide, and wherein the angular position of the longitudinal axis of the main body of the gripping and positioning tool is movable about a conical volume.

2. The kit according to claim 1, wherein said main body has ergonomic grooves to facilitate the handling of the tool even in the presence of fluids.

3. The kit according to claim 1, wherein said handle defines a T with said main body.

4. The kit according to claim 1, wherein the tool is made of a radiolucent material.

5. The kit according to claim 1, wherein the central axis of the spherical joint is coaxial with the longitudinal axis of the main body.

6. The kit of claim 1 wherein the main body, handle, and spherical joint are monolithically formed.

* * * * *